[19] United States Patent
Dietze et al.

[11] 4,152,425
[45] May 1, 1979

[54] GLUCOSE CONTAINING INFUSION SOLUTION

[75] Inventors: Günther Dietze; Matthias Wicklmayr, both of Munich, Fed. Rep. of Germany

[73] Assignee: THERA Gesellschaft für Patentverwertung mbH, Fed. Rep. of Germany

[21] Appl. No.: 861,368

[22] Filed: Dec. 16, 1977

[30] Foreign Application Priority Data

Dec. 17, 1976 [DE] Fed. Rep. of Germany ....... 2657381

[51] Int. Cl.$^2$ .............................................. A61K 37/00
[52] U.S. Cl. .................................................. 424/177
[58] Field of Search ........................................ 424/177

[56] References Cited
FOREIGN PATENT DOCUMENTS
1246315 10/1968 United Kingdom ..................... 424/177

*Primary Examiner*—Delbert R. Phillips
*Attorney, Agent, or Firm*—Burns, Doane, Swecker & Mathis

[57] ABSTRACT

There is disclosed an infusion solution which is particularly useful for intravenous feeding. This solution comprises from about 100 to about 600 grams of glucose per liter of solution and from about 10 to about 3,000 μ grams of at least one kinin per liter of solution.

10 Claims, No Drawings

GLUCOSE CONTAINING INFUSION SOLUTION

BACKGROUND OF THE INVENTION

1. Field of the Invention

This invention relates generally to infusion solutions. More specifically, this invention relates to glucose containing infusion solutions, which are especially useful for intravenous feeding.

2. Description of the Prior Art

Infusion solutions serve, among other purposes, to replenish part of the blood in the event of shocks resulting from various causes. Such solutions may also be used, by injection into arteries or veins, for the purpose of supplying the organism with substances needed by the body to maintain its metabolism or to overcome illnesses. These infusion solutions contain, especially when used for intravenous feeding, considerable quantities of glucose as well as amino acids, mineral salts and the like.

When the patient is subjected to situations of stress, such as during the post-surgical phase, or when the patient is infected, his metabolism will be affected adversely. This will be evidenced by an interruption in the utilization of the glucoses and an increased rate of decomposition of the proteins which are stored by, and are important to, the body and are thus used for the supply of energy. Because of this interruption in the glucose utilization, it has not been possible heretofore to feed a patient whose metabolism was not otherwise disturbed with glucoses exclusively because there was the danger of the presence of excessive glucose, causing a hyperglycemic coma. An admixture of insulin would not be practical in this situation because any dose of insulin would require a close control of the blood sugar level, especially because the reactions of patients to doses of insulin differ greatly.

It is for this reason that during intravenous feeding under these circumstances, the glucose heretofore has been combined with fructose or other sugar substitutes, or has been replaced completely by the same. However, it has been found that these substances also have side-effects, depending upon the quantity of the dosage being used. They necessitate up to four times as many phosphorylases in the liver, and the resulting greater consumption of the energy-rich phosphates may adversely affect the liver function. Furthermore, lactate will accumulate in these cases within the total organism, and on several occasions "lactate acidosis" has been observed under such circumstances. In this connection, see Mehnert et al "Diabetologie in Klinik und Praxis" [G. Thieme, Stuttgart (1974)], pp. 18 to 23. When such sugar substitutes are used, deposits of oxalate have been found in many different parts of the body.

The search has continued for improved glucose-containing infusion solutions. This invention was made as a result of that search.

OBJECTS AND SUMMARY OF THE INVENTION

Accordingly, a general object of the present invention is to avoid or substantially alleviate the above problems of the prior art.

A more specific object of the present invention is to provide a glucose-containing infusion solution.

Another object of the present invention is to provide a glucose-containing infusion solution which is especially useful for intravenous feeding.

Other objects and advantages of the invention will become apparent from the following summary and description of the preferred embodiments of the present invention.

The present invention provides a glucose containing infusion solution which is especially useful for intravenous feeding. This solution comprises from about 100 to about 600 grams of glucose per liter of solution and from about 10 to about 3,000$\mu$ grams of at least one kinin per liter of solution.

DESCRIPTION OF THE PREFERRED EMBODIMENTS

It has been found, surprisingly, that the glucose of the infusion solutions may be better tolerated and delivered to the tissue cells more quickly when one or more kinins are added to the solutions. Kinins are oligopeptides, the so-called local tissue hormones, tested especially for their vasodilating properties. These properties of the kinins cause a lowering of the blood pressure. The nonapeptide Brady kinin is a kinin having the following structure: ($NH_2$) arginine - proline - proline - glycine - phenylalanine - serine - proline - phenylalanine - arginine (COOH). The decapeptide kallidin is also a kinin which differs from the Brady kinin only in that it contains lysine residue at the amino end of the peptide chain. By the further addition of methionine, there is obtained a peptide called Meth-Lys-Brady kinin. This also has a kinin effect. In this connection, see Werle, "Angewandte Chemie," 1961, pp. 689 to 720; and "Arzneimittel," Volume 1, Verlag Chemie 1968, pp. 876 to 880.

The novel glucose-containing solutions, which are useful for infusions and especially for intravenous feeding, contain glucose and also may contain amino acids, sugar substitutes, and mineral salts and, in accordance with the present invention, from about 10$\mu$ gram to about 3,000$\mu$ grams, preferably from about 100 to about 1000$\mu$ grams, of kinins per liter of solution. It is possible to increase the content of glucose in comparison with the conventional concentration to 100 grams and even up to 600 grams per liter. These quantities of glucose, although relatively highly concentrated, are easily tolerated if kinins, such as Brady kinin, are present and are quickly absorbed from the blood stream by the tissue. The amino acids which may be mixed with the infusion solution which contains the glucose, are also made available more rapidly to the tissue cells by the Brady kinin and are thus utilized for the build-up of proteins, especially since the availability of a greater amount of glucose makes it unnecessary for the cells to utilize the amino acids for the energy metabolism.

Tests conducted on a resting forearm show a pronounced decrease of the glucose content in the blood flowing through the vein of the arm when only a fraction of 1$\mu$ gram of Brady kinin is mixed with a 10% solution of glucose and injected into the artery of the arm in the form of a 10 milliliter solution in comparison with a kinin-free solution. This illustrates the improved glucose absorption into the tissue of the arm and the muscular system of the hand when the solution of the present invention is employed. Since the effect of this decrease in the glucose level of the blood by the kinin admixture occurs so quickly, it may be assumed that this is caused not by an intensification of the decomposition of the glucose or the metabolism within the cell but by a more rapid penetration of the muscular cell.

This novel anti-diabetogeneous effect of the kinins, when added to glucose-containing infusions, is particularly surprising since kinins are known, in addition to their influence on the circulatory system and on the contraction of the relaxed muscular system, to cause vehement local pain reactions if injected subcutaneously even in minimum doses.

It is also known from the published German application 2 357 507 that the kinins, such as Brady kinin and kallidin, will further the mobility of the spermatozoa, and are therefore recommended as means for the improvement of fertility, for example, by means of artificial impregnation.

The addition of kinins to the infusion solutions in accordance with the present invention makes possible an improvement in the glucose supply to cells which have been damaged by stress or shock. Such cells include, for example, heat muscle cells which have been damaged by infarction. This applies especially to persons who have diabetes. Such persons heretofore usually had to be given sugar substitutes, for example, sugar alcohols such as xylitol and sorbitol because of their limited utilization of glucose. For such diabetic patients it is also possible to save or replace insulin by administering the infusions proposed by the invention. This insulin reduction is especially important if the patient is allergic to insulin. The improved movement of the glucose into the muscular cells enhance the ability of the tissue to recover and hence enhances the ability of the entire organism to recuperate. The resistance of the organism to infections is also increased.

Imbalances in the metabolism which might occur because of an increase in the insulin-counteracting hormones, for example, in stress situations after surgery, will be leveled off without the need for additional doses of insulin. If necessary, relatively large quantities of glucose may be introduced into the organism without creating a hyperglycemic coma. The caloric requirement may be met sufficiently by the glucose so that sugar substitutes need to be given, if at all, in small quantities, thus making the amino acids of the infusion solutions fully available for the regenerative protein build-up.

The kinins, being relatively low-molecular oligopeptides having from 9 to 11 amino acids and easily manufactured synthetically, do not have any allergic effects. The solutions may also be sterilized without difficulty and may be stored practically for any length of time at normal temperatures, preferably in a refrigerator. By the method described by Rasio et al, "Diabetologica," Volume 8, pp. 244 to 249 (1972), it is possible to test and analyze the absorption of glucose by the muscular cells of the human forearm, by infusing a glucose solution into the intrabrachial artery of the arm, and measuring the reduction in the glucose content of the blood flowing back through the veins.

Table I below lists the values of the glucose assimilation in micromoles of glucose for every 100 grams of tissue per minute ± SEM, computed from four tests on six male persons for each test. Glucose solutions of 10% by weight were used, either without Brady kinin or with a content of 500µ grams of the Brady kinin per liter. In each case, the solutions were infused into the artery of the arm at a rate of 0.2 milliliters per minute.

TABLE I

| | Infusion (10% by weight of glucose solution at 0.2 milliliters/minute) | | | |
|---|---|---|---|---|
| Basal | | 5 minutes | 15 minutes | 25 minutes |
| without kinin | 0.956 ± 0.13 | 1.82 ± 0.28 | 2.15 ± 0.24 | 2.37 ± 0.29 |
| with kinin | 1.052 ± 0.18 | 2.58 ± 0.39 | 4.12 ± 0.38 | 4.40 ± 0.41 |

The results of these tests demonstrate that when the composition of the present invention is employed, there is almost a doubling of the glucose absorption from the blood stream by the muscular tissue of the human forearm.

In order to demonstrate the intensified glucose utilization when kinin is admixed with glucose, it is also possible to employ the glucose-assimilation test. If patients are infused intravenously with a large quantity of glucose within a time period of six minutes, the glucose level in the blood of the patient will rise quickly and then drop again gradually. It is known that conclusions concerning the utilization of the glucose within the tissues of the body cannot be drawn from the maximum value of the blood sugar level attained but only from the rate of the blood sugar drop. According to Franckson, "Metabolism", volume 11, p. 482 (1962), the glucoseassimilation coefficient $k_G$ may be computed from the length of time T, at which the glucose level has dropped to one half of its maximum value, by use of the formula $k_G = 69.3/T$. If the $k_G$ value is lower than 1.0, there is a disorder in the utilization of glucose, such as diabetes mellitus. If the value ranges from 1.0 to 1.2, there is reason to assume the presence of diabetes while values above 1.2 indicate proper glucose assimilation.

Two groups (A and B) of 12 patients each of approximately the same age which had been in surgery under similar conditions (stomach resection), received during the first and second days after surgery, 150 milliliters of infusion solutions containing 25% by weight glucose (corresponding to 37.5 grams of glucose) within a period of six minutes. One group (A) received the infusion solution with kinin as listed in Example 1 hereinbelow on the first day and on the second day the control solution described in Example 1 but without kinin. The sequence was reversed for the second group (B), i.e., this group received the control solution on the first day, and the kinin-containing infusion solution of the present invention on the second day after surgery.

The results of the evaluation of the glucose assimilation test are listed in Table II hereinbelow as average values ± SEM of the glucose assimilation coefficient $k_G$. The statistical differences between the average values are determined in accordance with the "Student-T-Test". Significant differences within one group are denoted by a) and between the groups by b). At the same time, values are determined for the urinary glucose eliminations during the test.

TABLE II

| | Group A | |
|---|---|---|
| | first day (solution with kinin) | second day (solution w/o kinin) |
| $K_G$ | 1.54 ± 0.10 | 1.24 ± 0.19 a) |
| urinary glucose in grams | 0.597 ± 0.24 | 0.85 ± 0.34 |
| | Group B | |
| | first day (solution w/o kinin) | second day (solution with kinin) |
| $k_G$ urinary | 0.83 ± 0.28 b) | 1.25 ± 0.33 a) |

TABLE II-continued

| | | |
|---|---|---|
| glucose in grams | 1.007 ± 0.18 | 0.825 ± 0.25 |

These results indicate that with both groups there is a distinct improvement in the glucose utilization at the time of use of the infusion solution of the present invention. Since the urinary elimination is lower whenever the infusion solution with kinin is used, the intensified drop of the glucose level indicates an improvement in the glucose assimilation due to the presence of the kinin in the infusion solution.

The admixture of kinin to amino-acid-containing solutions, used for the intravenous feeding of patients after surgery, results further in a lowering of the decomposition of the protein present within the body, and in an improvement of the amino acid utilization. Two groups of patients which had been in surgery under identical conditions were given infusions of one liter each of a solution of the present invention as described in Example 3 hereinbelow and another control solution of similar composition but without any kinin. One solution was applied continuously for 12 hours dropwise, and the other solution was then applied dropwise for 12 hours. The nitrogen elimination in the urine was determined in each case. Group A consisted of four, and group B of five patients who had stomach resections. The average values ± SEM of the nitrogen elimination, given in grams, are listed in Table III, with the statistical differences determined, as in case of the tests shown by Table II, in accordance with the "Student-T-Test", and with the significant difference within one group denoted by a), and between the groups denoted by b).

TABLE III

| | Group A | |
|---|---|---|
| | 12 hours after surgery | 12 hours subsequent |
| urine | (solution with kinin) | (solution without kinin) |
| nitrogen | 2.16 ± 0.24[b)] | 3.59 ± 0.38[a)] |
| in grams | | |
| | Group B | |
| | 12 hours after surgery | 12 hours subsequent |
| urine | (solution without kinin) | (solution with kinin) |
| nitrogen | 3.81 ± 0.41 | 2.91 ± 0.27[a)] |
| in grams | | |

The nitrogen elimination in the urine is reduced significantly in both groups whenever the infusion solution contains the kinin in accordance with the present invention, thus indicating an improvement in the amino acid utilization.

It is also found that the decomposition of the kinins which occurs within the organism may be inhibited significantly by the use of phenothiazines, for example, a chloropromazine such as 2-chloro-10-(3-dimethylamino-propyl)-phenothiazine. This is unexpected and surprising because the phenothiazines were known heretofore only as substances having an anti-depressive effect. This fact could cause one to conclude, however, that they could affect certain oligopeptides which influence the metabolism and would indirectly, i.e., by inhibiting the decomposition of the kinins, improve the glucose assimilation of the tissue.

Therefore, in a preferred embodiment of the present invention, there is added to the kinin-containing glucose infusion solution from about 5 to about 50 milligrams of phenothiazine per liter of solution, in addition to any other additives which might be present, such as amino acids, sugar alcohols, mineral salts and the like.

When such a glucose solution containing kinins and phenothiazine is used, its more lasting effect becomes apparent by an increase in the glucose assimilation coefficient $k_G$. This effect is strong even on the second day as noted in the tests for Group A which are described in Table II.

The present invention is further illustrated by the following examples. All parts and percentages in the examples as well as in the specification and claims are by weight unless otherwise specified.

EXAMPLE 1

By dissolving 250 grams of glucose and 500μ grams of Brady kinin in water (aqua pro injectione) up to a total volume of 1,000 milliliters, an infusion solution for the supply of calories is obtained which is administered at an infusion rate of 500 milliliters in three hours without causing an undesirable increase in the blood sugar level.

EXAMPLE 2

One hundred fifty grams of glucose, 50 grams of fructose, 50 grams of xylitol and 500μ grams of kallidin are mixed with water (aqua pro injectione) to a total volume of 1,000 milliliters. The solution is sterilized by heating it to 110° C. for 30 minutes in a closed bottle. The solution serves as a supply of calories.

EXAMPLE 3

The following substances are dissolved in water (aqua pro injectione) to a total volume of 1,000 milliliters:
  100.0 grams of glucose,
  2.2 grams of l-isoleucine
  3.4 grams of l-leucine
  2.7 grams of l-lysine
  2.4 grams of l-methionine
  2.3 grams of l-phenylalanine
  1.9 grams of l-threonine
  0.7 grams of l-tryptophan
  2.0 grams of l-valine
  4.3 grams of l-arginine
  2.1 grams of l-histidine
  1.1 grams of l-aspartic acid
  6.0 grams of l-glutamic acid
  3.8 grams of glycine
  6.5 grams of l-alanine
  0.4 grams of l-tyrosine
  6.0 grams of l-proline
  2.0 grams of l-serine
  1.5 grams of l-asparagine
  0.2 grams of l-cystine
  1.2 grams of l-ornithine
  1.71 grams of KOH
  1.12 grams of Magnesium-acetate . $4H_2O$
  1.55 grams of NaOH
  1.99 grams of l-malic acid
  500μ grams of Brady kinin This solution is then sterilized in the usual manner. The solution is to be used for the partial intravenous supply of nourishment, containing further a supply of amino acids for the protein build-up and is administered at an infusion rate of 500 milliliters in three hours.

EXAMPLE 4

The following substances are dissolved in water (aqua pro injectione) to a total volume of 1,000 milliliters:
  100.0 grams of glucose 1.0 grams of l-isoleucine
1.6 grams of l-leucine
1.2 grams of lysine
1.1 grams of methionine
1.1 grams of phenylalanine
0.9 grams of l-threonine
0.3 grams of l-tryptophan
1.0 grams of l-valine
2.1 grams of l-arginine
1.0 grams of l-histidine
0.5 grams of l-aspartic acid
3.0 grams of l-glutamic acid
1.9 grams of glycine
3.2 grams of l-alanine
0.2 grams of l-tyrosine
3.0 grams of l-proline
0.9 grams of l-serine
0.7 grams of l-asparagine
0.1 grams of l-cystine
0.5 grams of l-ornithine
0.85 grams of KOH
0.56 grams of Magnesium-acetate . $4H_2O$
0.77 grams of NaOH
0.99 grams of l-malic acid
25.0 grams of fructose
25.0 grams of xylitol
500$\mu$ grams of Brady kinin For complete intravenous nourishment. For sterilization and administration rate see Example 3.

EXAMPLE 5

Example 3 is repeated with the exception that 15 milligrams of 2-chloro-10-(3-dimethylaminopropyl)-phenothiazine are added to the solution prior to sterilization.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. A glucose-containing infusion solution consisting essentially of from about 100 to about 600 grams of glucose per liter of solution, and from about 10 to about 3,000 grams of at least one kinin per liter of solution.

2. The infusion solution of claim 1, wherein said solution contains from about 100 to about 1,000$\mu$ grams of kinins per liter.

3. The infusion solution of claim 1, wherein said kinin is Brady kinin.

4. The infusion solution of claim 2, wherein said kinin is Brady kinin.

5. The infusion solution of claim 1, wherein said solution contains from about 5 to about 50 milligrams per liter of solution of phenothiazines.

6. The infusion solution of claim 2, wherein said solution contains from about 5 to about 50 milligrams per liter of solution of phenothiazines.

7. The infusion solution of claim 3, wherein said solution contains from about 5 to about 50 milligrams per liter of solution of phenothiazines.

8. The infusion solution of claim 1 wherein said solution contains amino acids.

9. The infusion solution of claim 8, wherein said solution contains sugar substitutes.

10. The infusion solution of claim 9, wherein said solution contains mineral salts.

* * * * *

UNITED STATES PATENT AND TRADEMARK OFFICE
CERTIFICATE OF CORRECTION

PATENT NO. : 4,152,425
DATED : May 1, 1979
INVENTOR(S) : Gunther Dietze et al

It is certified that error appears in the above–identified patent and that said Letters Patent are hereby corrected as shown below:

In Claim 1, line 4, before "grams" insert the symbol -- $\mu$ --.

Signed and Sealed this

Ninth Day of June 1981

[SEAL]

Attest:

RENE D. TEGTMEYER

Attesting Officer    Acting Commissioner of Patents and Trademarks